United States Patent
Koehler et al.

(10) Patent No.: US 7,238,757 B2
(45) Date of Patent: Jul. 3, 2007

(54) OXYGEN-CONTAINING ORGANOALUMINIUM COMPLEXES AS COCATALYSTS

(75) Inventors: Katrin Koehler, Goettingen (DE); Eike Poetsch, Muehltal (DE); Jens Eichhorn, Reinheim (DE); Herbert Schumann, Berlin (DE); Birgit Wassermann, Berlin (DE); Sebastiain Dechert, Berlin (DE); Markus Hummert, Berlin (DE); Stefan Schutte, Berlin (DE); Walter Kaminsky, Pinneberg (DE); Andrea Eisenhardt, Vechta (DE); Manfred Arnold, Leissling (DE)

(73) Assignee: Merck Patent Gesellschaft, Darmstadt (DE)

( * ) Notice: Subject to any disclaimer, the term of this patent is extended or adjusted under 35 U.S.C. 154(b) by 0 days.

(21) Appl. No.: 10/527,818

(22) PCT Filed: Sep. 13, 2002

(86) PCT No.: PCT/EP02/10300

§ 371 (c)(1),
(2), (4) Date: Mar. 20, 2006

(87) PCT Pub. No.: WO2004/033466

PCT Pub. Date: Apr. 22, 2004

(65) Prior Publication Data

US 2006/0199926 A1    Sep. 7, 2006

(51) Int. Cl.
*C08F 4/642* (2006.01)
*C07F 5/06* (2006.01)

(52) U.S. Cl. .................. 526/124.3; 526/348; 526/352; 502/115; 502/132; 556/170

(58) Field of Classification Search ................ 502/115, 502/132; 526/120.2, 124.3, 348, 352; 556/170
See application file for complete search history.

(56) References Cited

U.S. PATENT DOCUMENTS 3,309,347 A    3/1967  Coover, Jr. et al.
6,596,890 B1   7/2003  Poetsch et al.

FOREIGN PATENT DOCUMENTS

EP    0 919 557 A1    6/1999
FR    1410868         9/1965
GB    889444          2/1962

OTHER PUBLICATIONS

Blum et al.: "Palladium-Catalyzed Methylation of Aryl and Vinyl Halides by Stabilized Methylaluminum and Methylgallium Complexes" Journal of Organic Chemistry, American Chemical Society, Easton, US Bd. 62, Nr. 25, 1997, XP002096902.
Boker et al.: "Halides of o-substituted aryl-aluminum compounds with coordination number four and five" Main Group Metal Chemistry, Tel Aviv, IL, Bd. 21, Nr. 9, 1998, XP002096900.
Gelman D et al: "Dichlorobis (triphenylphosphine) nickel-catalyzed cross-coupling of aryl chlorides with intramolecularly stabilized group 13 metal alkylating reagents" Tetrahedron Letters, Elsevier Science Publishers, Amsterdam, NL, Bd. 41, Nr. 39, Sep. 23, 2000 XP004217349.
Database Registry "Online! Chemical Abstracts Service; 1973 Database accession No. RN: 13107-21-6 XP002240431.

*Primary Examiner*—Caixia Lu
(74) *Attorney, Agent, or Firm*—Millen, White, Zelano & Branigan, P.C.

(57) ABSTRACT

Disclosed are compounds of formula (I)

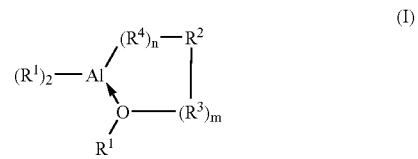

Figure 1:
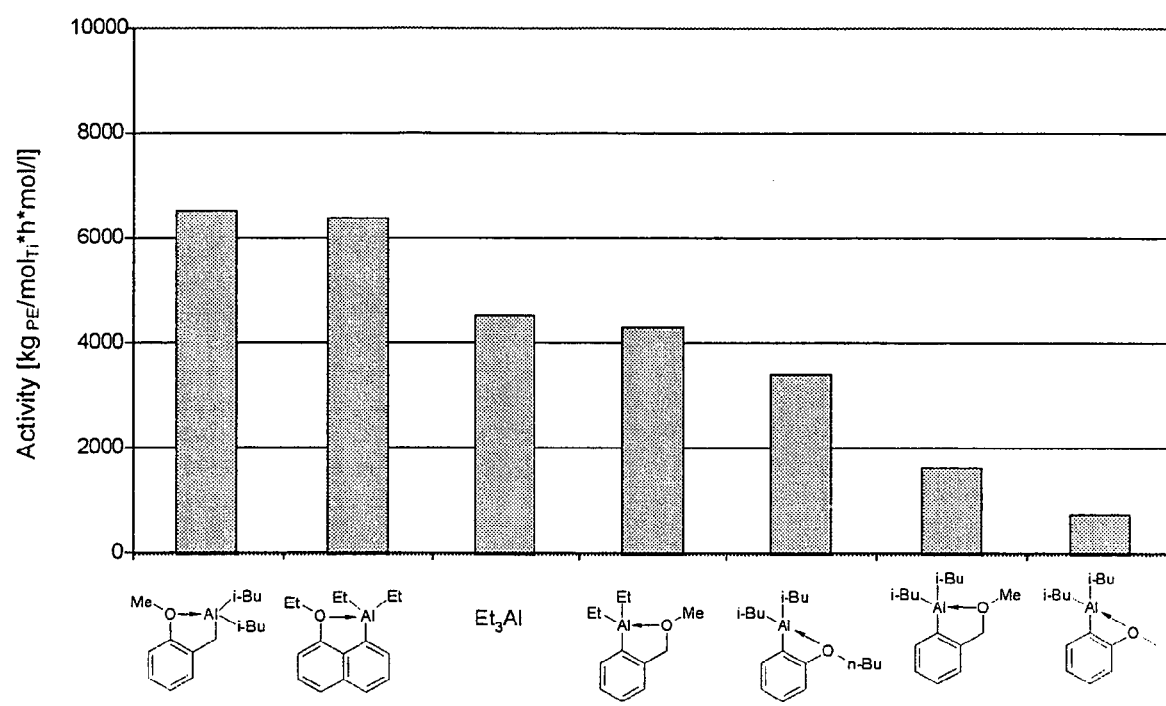

which compounds are useful as cocatalysts in olefinic polymerisation reactions, e.g., as Ziegler-Natta catalysts.

14 Claims, 1 Drawing Sheet

OXYGEN-CONTAINING ORGANOALUMINIUM COMPLEXES AS COCATALYSTS

The present invention relates to oxygen-containing organoaluminium complexes of the general formula (I)

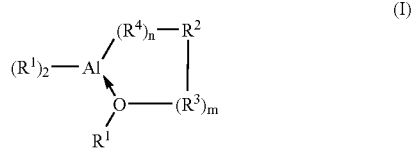

in which $R^1$, independently of one another, denote branched or unbranched $C_1$–$C_7$-alkyl, -cycloalkyl, -alkenyl, -cycloalkenyl, -aryl or -alkynyl;

$R^2$ denotes unsubstituted, mono- or polyalkylated and/or mono- or polyfluorinated aromatic hydrocarbons from the group

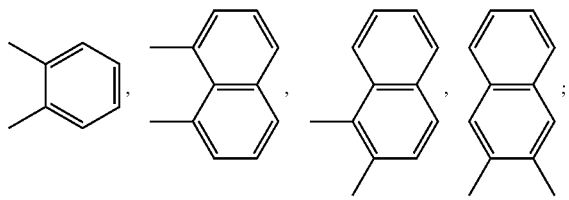

$R^3$, $R^4$, independently of one another, denote $CH_2$, $CF_2$ or $C(R^1)_2$;

independently of one another m denotes 0, 1, 2 n denotes 0, 1, 2.

These compounds can be employed as cocatalysts in olefinic polymerisation reactions, where they have improved properties compared with conventionally employed compounds.

Common coordination catalyst systems are extraordinarily versatile catalysts which are employed in chemical reactions of and with olefinically unsaturated compounds. These are, in particular, processes for the preparation of olefin polymers by coordination polymerisation and the metathesis of alkenes or alkynes. Of considerable industrial importance is the preparation of various polyethylenes for various applications, for example high density polyethylene (HDPE) or particularly low density polyethylene (LLDPE), and of polymers and copolymers of ethylene, propylene or other 1-alkenes and alkynes. Catalysed metathesis can be employed for the specific preparation of higher unsaturated hydrocarbon compounds from asymmetrical alkenes or alkynes and of long-chain unsaturated hydrocarbons from unsaturated cyclic hydrocarbon compounds. The long-chain unsaturated hydrocarbons are used, for example, in the preparation of elastomers. In addition, coordination catalysts are used in further reactions, such as, for example, in the hydrogenation of alkenes or in organometallic syntheses.

According to the scientific knowledge to date on the mechanism of action of coordination catalysts, it is assumed that a transition-metal compound in each case forms the catalytically active centre to which the olefinically unsaturated compound binds coordinatively in a first step. The olefin polymerisation takes place via coordination of the monomers and a subsequent insertion reaction into a transition metal-carbon or transition metal-hydrogen bond. The presence of organometallic compounds in the coordination catalyst systems or during the catalytic reaction is necessary in order to activate the catalyst by reduction and optionally alkylation or the formation of a complex system (cation/anion) or to maintain its activity. These compounds are therefore also known as cocatalysts. The compound containing the catalytically active transition-metal atom is known as the primary or pre-catalyst.

Coordinative polymerisation using complex initiator systems has achieved considerable industrial importance in recent years, particularly for the polymerisation of ethylene at low pressures. In the USA alone, more than $8 \cdot 10^9$ metric tons of PE were produced in 1995. (S. W. Bigger, Eur. Polym. J. Vol. 32, No. 4, pp. 487, 1996)

The most important catalysts in industry in this area are the so-called Ziegler-Natta catalysts. This is the name given to systems which consist of a combination of compounds of metals from sub-group IV–VII of the Periodic Table of the Elements with, for example, alkyl or aryl compounds or hydrides of the elements from main groups I–III. Typical Ziegler catalysts are formed, for example, on reaction of $TiCl_4$ with Et3Al; $TiCl_3$ with $AlEt_2CL$. These systems are heterogeneous catalysts; they are formed as fine suspension in an organic solvent (for example heptane).

The most important, preferably used alkylaluminium compounds are $AlEt_3$, Al-i-$Bu_3$, $AlEt_2Cl$, $AlEtCl_2$, $AlEtCl_2$ and $AlEt_2OR$, all of which are very sensitive to atmospheric oxygen and moisture and are pyrophoric and are therefore difficult to handle. Instead of the titanium chlorides, compounds of vanadium and chromium, in specific applications also molybdenum, cobalt, rhodium and nickel, are of particular interest. Instead of the alkylaluminium compounds, numerous other organometallic compounds, particularly sodium, lithium and cadmium, are described as effective in combination with titanium compounds. (H. J. Sinn et al., Polymerisation und Insertionsaktivität von Aluminiumtrialkylen und Ziegler-Natta Katalysatoren [Polymerisation and Insertion Activity of Trialkylaluminium Compounds and Ziegler-Natta Catalysts], Angew. Chem. 72 (1960) 522)

Industrially important solution polymerisation processes for the preparation of HDPE are, for example, the Dow process.

In this, a mixture of $TiCl_x$ and $AlR_3$ is prepared in hydrocarbons ($C_8$–$C_9$) at a pressure p>10 bar and a reaction temperature T>180° C. The activity in the continuous process (140° C., 30 bar; $TiCl_4$: $AlR_3$=1:5) is 6.323 g of PE/h. (Dow, U.S. Pat. No. 3,491,073, 1970)

In a Du Pont process, Ti/V halides are produced with $AlR_3$ in cyclohexane at pressures of 200 bar and a temperature of 180–270° C. The activity is 20–50 kg of PE/g of metal hour; the molecular weight, determined viscosimetrically, is Mη=1.8·10 g/mol. (Du Pont, U.S. Pat. No. 2,862,917, 1958; J. P. Forsman, Hydrocarbon Processing, 51(11), 130(1972)

Industrially important suspension polymerisation processes for the preparation of HDPE are, for example, the Mitsubishi process. In this, HDPE is produced in a stirred reactor using a titanium catalyst in n-hexane at 5–10 bar and 30–90° C. (A. Kageyama, Hydrocarbon Processing 51(7), 115(1972), or the Montedison process. The Montedison process is carried out in a stirred reactor using titanium catalysts in benzine at 1–15 bar and 50–100° C. The activity is 200 kg of PE/g of Ti. (A. Heath, Chemical Engineering (April 3) 66(1972)

After this heterogeneity, in particular, was made responsible for the catalytic activity ("catalytic surface area") in the initial phase, soluble (homogeneous) systems which had approximately the same activity were also subsequently found.

Thus, for example, the combination of bis(cyclopentadienyl)titanium dichloride ($Cp_2TiCl_2$) or vanadyl chloride ($VOCl_3$) and diethylaluminium chloride ($Et_2AlCl$) or alumoxane ($[-OAl(CH_3)-]_n$) gives a homogeneous Ziegler catalyst. A further important homogeneous catalyst system is: $Cp_2ZrMe_2$/alumoxane (homogeneous).

$MgCl_2$-bound $TiCl_4$ catalyst systems were discovered in 1970 and are called second generation catalyst systems or "leave-in" catalysts. An example of this heterogeneous system is: $MgCl_2$/ester/$TiCl_4AlR_3$. The catalyst activity is 200 kg of PE/g of Ti h. (A. D. Jenkins, A. Ledwith; Reaktivity, Mechanism and Structure in Polymer Chemistry).

All these known catalyst systems harbour the disadvantages that they can only be employed at elevated temperature and a pressure above 10 bar, with nevertheless a satisfactory catalyst activity not being achieved in all cases.

Practical use of these catalysts and related types in the great variety of process variants that have been developed can give products having in some cases extremely different properties. In the case of olefin polymers, which are of generally known importance as materials, usability and range of applications depend, owing to the properties, firstly on the type of parent monomers or on the choice and ratio of the comonomers and the typical physical parameters characterising the polymer, such as mean molecular weight, molecular weight distribution, degree of branching, degree of crosslinking, crystallinity, density, presence of functional groups in the polymer, etc., and secondly on properties caused by the process, such as content of low-molecular-weight impurities, presence of catalyst residues and ultimately on the costs.

In order to assess the performance of a coordination catalyst system, further factors besides the achievement of the desired product properties, such as the activity of the catalyst system, i.e. the amount of catalyst necessary for economical conversion of a predefined amount of olefin, the product conversion per time unit and the product yield, the loss of catalyst and the reusability of the catalyst, are crucial. Catalyst systems having the highest possible productivity, but also having high specificity in favour of a low degree of branching and high stereoregularity of the polymer are therefore sought.

However, the question of stability and handleability of the catalyst or its components is also fundamental. Virtually all known coordination catalysts based on earlier transition-metal compounds are extremely air- and Moisture-sensitive. Ingress of (atmospheric) oxygen and/or water reduces the activity of or irreversibly destroys the coordination catalysts. The coordination catalysts must therefore be protected strictly against ingress of air and moisture during preparation, storage and use, which naturally makes handling more difficult and increases the requisite complexity.

Conventional catalyst systems are also sensitive to substances which contain electron-rich elements, such as, for example, oxygen or nitrogen, in the molecule. Compounds such as alcohols and amines or also polar monomers, which may be of interest as comonomers or additives for the polymer, deactivate the catalyst.

Even more sensitive in this respect and therefore still more difficult to handle are the organometallic compounds to be employed as activators or cocatalysts, such as, in particular, the alkylaluminium compounds predominantly used for this purpose. These very compounds, owing to their extreme sensitivity and spontaneous combustibility, represent a serious problem in practice.

The object of the present invention therefore consists in finding less sensitive organoaluminium compounds which are suitable as activating component in catalyst systems and exhibit higher activity or productivity compared with the prior art in their use in these catalyst systems. These compounds should furthermore have lower sensitivity and thus facilitate easier handleability.

The object is achieved by novel compounds according to Claim 1 of the general formula (I)

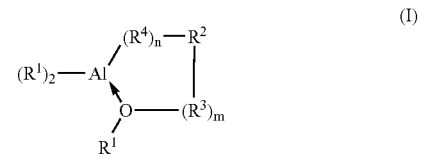

in which $R^1$, independently of one another, denote branched or unbranched $C_1-C_7$-alkyl, -cycloalkyl, -alkenyl, -cycloalkenyl, -aryl or -alkynyl;

$R^2$ denotes unsubstituted, mono- or polyalkylated and/or mono- or polyfluorinated aromatic hydrocarbons from the group

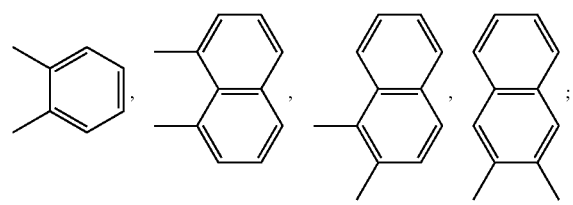

$R^3$, $R^4$, independently of one another, denote $CH_2$, $CF_2$ or $C(R^1)_2$;

independently of one another m denotes 0, 1, 2 n denotes 0, 1, 2.

These compounds can serve as cocatalysts in olefinic polymerisation reactions. In particular, these compounds having improved properties can be employed for the preparation of novel Ziegler-Natta catalysts having higher activities and productivities compared with the prior art using conventional Ziegler-Natta catalysts with $AlEt_3$ as cocatalyst, or novel coordination catalyst systems which have higher activities than conventional Ziegler-Natta catalysts, even at low temperatures, such as 60° C., and a pressure of 2 bar.

It has been found that intramolecularly stabilised organoaluminium compounds of the formula (I) are eminently suitable as components in coordination catalyst systems.

The present invention therefore relates to the use of intramolecularly stabilised organoaluminium compounds of the formula (I) as components in coordination catalyst systems and to coordination catalyst systems which comprise compounds of the general formula (I).

The invention also relates, in particular, to the use of the compounds of the formula (I) as components in Ziegler-Natta catalysts.

Coordination catalyst systems which comprise compounds of the general formula (I) are, in accordance with the invention, in the form of a combination with transition-metal compounds from sub-group IV to VIII of the Periodic Table of the Elements.

Combinations according to the invention of the coordination catalyst systems which comprise compounds of the general formula (I) with transition-metal compounds are, in particular, those in which compounds from the group $TiCl_4$ and $VCl_4$ are present.

The invention also relates to processes for the preparation of polymers by polymerisation in which the above-mentioned coordination catalyst systems are used. In particular, these are processes for the preparation of polyethylene and polypropylene, preferably processes for the preparation of high-molecular-weight polyethylene and polypropylene.

Compounds of the formula (I) according to the invention have a cyclic structure in which aluminium as an element from group IIIa and oxygen as an element from group VIa of the Periodic Table of the Elements in each case represent a member of the ring system. In compounds of the formula (I), directly adjacent, covalently bonded atoms carbon atoms are present on the aluminium. The oxygen atom is coordinatively bonded to aluminium and covalently bonded to 2 carbon atoms.

Alkyl substituents may in such cases be straight-chain or branched having 1–7 C atoms. They may also be part of a cyclic ring. They are preferably alkyl groups having 1–4 C atoms from the group methyl, ethyl, n- and i-propyl, n-, i- and t-butyl. Corresponding alkyl groups are represented in the formula (I) by the symbol $R^1$.

Suitable aryl substituents are both phenyl and also naphthyl. Aryl substituents are part of the cyclic ring. They may be bonded to the oxygen and/or to the aluminium atom directly or via an alkyl spacer having 1 or 2 carbon atoms. However, aryl substituents may also be mono- or polyalkylated or -fluorinated hydrocarbons, in particular of phenyl and naphthyl. Corresponding aryl groups are represented by the symbol $R^2$ and also $R^1$.

Suitable compounds of the formula (I) have four substituents on a central aluminium atom, of which the oxygen is, with great probability, coordinatively bonded and contributes to the stabilisation of the compound. More precise details of the bonding ratios cannot be given.

Compounds according to the invention can be prepared by methods known to the person skilled in the art for the preparation of organometallic compounds. Processes for the preparation of such compounds are described, for example, in G. Bähr, P. Burba, Methoden der organischen Chemie [Methods of Organic Chemistry], Vol. XII/4, Georg Thieme Verlag, Stuttgart (1970). To be precise, these compounds can be prepared under the reaction conditions which are known and suitable for the said reactions. However, use can also be made here of variants known per se which are not described here in greater detail. Further details on the synthesis are revealed by DE-A 38 17 090 A1 and DE-A 37 26 485 A1 or Chem. Ber. 124, 1113–1119, (1971). The technical teaching given by these documents is thus part of the disclosure content of the present description.

In particular, the compounds of the general formula (I) according to the invention can be prepared by a process in which an alkoxyaryl-metal compound, such as, for example, alkoxyaryllithium or an alkoxyaryl-Grignard compound, is reacted with a dialkylaluminium chloride, where the alkoxyarylmetal compound to dialkylaluminium chloride molar ratio is 1:1.

The process is preferably carried out by a) mixing an alkoxyarylmetal compound, such as, for example, alkoxyaryllithium or an alkoxyaryl-Grignard compound, suspended in a hydrocarbon or diethyl ether, with an equimolar amount of a dialkylaluminium chloride, dissolved in a suitable hydrocarbon, at a temperature of +20 to −78° C., b) stirring the mixture at a temperature of 20 to 80° C. for 2 to 60 hours, removing the solvent, and separating off the desired reaction product by distillation or crystallisation.

Suitable solvents for carrying out the process may be hydrocarbons or aprotically polar solvents, such as, for example, diethyl ether or tetrahydrofuran. The hydrocarbons may be both aliphatic and also aromatic hydrocarbons. The suitable hydrocarbons include, inter alia, pentane, hexane, heptane, toluene. Further suitable hydrocarbons are known to the person skilled in the art and can be selected depending on the starting compounds.

After the reaction, the product prepared is worked up in a manner known per se. After the solids formed have been separated off, the work-up is preferably carried out by distillation or crystallisation.

Surprisingly, it has now been found that the compounds according to the invention are particularly suitable as components in coordination catalyst systems. Using the compounds according to the invention in coordination catalyst systems for polymerisations, in particular for olefin polymerisations, in which transition-metal compounds from sub-group 4 to 8, in particular compounds of titanium, are used, higher activities or productivities compared with the prior art have been obtained. On the one hand catalyst systems having particularly high activity, stability and service life and on the other hand polymerisation products having high molecular weights and at the same time a uniform structure are obtained.

It has been found that the compounds according to the invention are fairly stable to oxygen, in particular the oxygen in air, and to the influence of moisture. This also applies to the coordination catalysts prepared with the aid of these compounds. Furthermore, corresponding coordination catalyst systems have particularly high stability under reaction conditions. They have a significantly lower tendency towards deactivation by compounds having free electron pairs, in particular such compounds which contain hetero atoms, such as sulfur, oxygen, nitrogen or phosphorus. The catalyst systems according to the invention have very particularly advantageous properties in polymerisation reactions, particularly in olefin polymerisation reactions.

Thus, it has been found that very particularly good results are obtained with $TiCl_4$ as catalyst, supported on $MgCl_2$, and the compounds according to the invention. Particularly good results are achieved by systems in which $TiCl_4$ is activated by oxygen-stabilised organoaluminium compounds in which an aromatic ring is located in the vicinity of the aluminium or the oxygen atom in the cyclic ring. The increase in activity by the compounds present in Table 1 (2-methoxybenzyl)diisobutylaluminium and (8-ethoxynaphth-1-yl)diethylaluminium, which, in the presence of $MgCl_2/TiCl_4$, gives high-molecular-weight products with higher yields (6100 kg of $PE/mol_{Ti}*h*c_{ethene}$) than the conventional Ziegler-Natta catalyst $MgCl_2/TiCl_4$ and $AlEt_3$ (4500 kg of $PE/mol_{Ti}*h*c_{ethene}$), is outstanding. Improved properties are likewise achieved if the compounds (2-methoxymethylphen-1-yl)diethylaluminium, (2-butoxyphen-1-yl)diisobutylaluminium are used.

With the aid of all catalyst systems tested in accordance with the invention, very high-molecular-weight polyethylene and polypropylene was obtained in extremely high yields. This means that termination reactions of the polymer chains by the catalytic centre are low during the polymerisation and that the entire catalyst system is very stable to impurities and other external influences.

Overall, the coordination catalyst systems according to the invention have particularly high specificity in the polymerisation of olefins, and products having high molecular weights and narrow molecular weight distributions are obtained. Although this is also dependent on the reaction management and the reactants employed, it belongs, however, to the standard methods of a person skilled in the art, if necessary, to optimise the reaction conditions.

The use in accordance with the invention of the compounds of the formula (I) as activating components in coordination catalyst systems takes place entirely analogously and in replacement of the organometallic compounds conventional hitherto, in particular the less stable and hazardous alkylaluminium compounds.

Due to the high activity of the catalyst systems, more product is formed with an employed amount of catalyst or the catalyst amount can be significantly reduced. The latter has the consequence that significantly less catalyst remains in the product. In addition, the costs can be reduced owing to lower catalyst consumption. Although the costs are influenced by a series of further factors, such as qualitative and quantitative composition of the catalyst systems, monomers employed, reaction conditions and procedure during the polymerisation, the catalyst used plays, however, a not insignificant role, merely through requisite protective measures for maintaining the activity. Owing to the wide variety of oxygen-stabilised organoaluminium compounds according to the invention, the person skilled in the art can readily determine and optimise the catalyst system which is most suitable for his purposes with the aid of routine experiments.

As already stated above, the compounds of the formula (I) according to the invention are very stable compounds with the aid of which likewise very stable coordination catalyst systems are advantageously obtained, making their preparation, storage and use significantly less problematic than in the case of systems known to date. In particular, the complex complete exclusion of oxygen, air and moisture in the solvents, monomers and protective gases employed in the polymerisations can be omitted.

The catalysts are prepared and used in a manner known per se, as is usual for the particular system and the particular use. In general, the suspension process is used in the polymerisation of olefins and in metathesis using heterogeneous catalysts. To this end, firstly the support-bound precatalyst is prepared from the catalytic transition-metal compound and a finely divided support material, this precatalyst is, if necessary, activated or preactivated in the conventional manner and suspended in a solvent, for example in an alkyl hydrocarbon, such as pentane, hexane, heptane or octane. The cocatalyst is added, as otherwise also usual, immediately before the reaction of the monomers or "in situ" in the presence thereof. The reaction is controlled and the reaction products isolated and worked up likewise in an entirely analogous manner.

As already mentioned earlier, all process steps can be carried out significantly more easily and under significantly less strict protective and safety measures owing to the increased stability of the donor-stabilised organoaluminium compounds and the considerably reduced sensitivity of the catalyst compounds obtained.

The present invention therefore makes accessible novel catalyst systems having advantageous properties, such as, for example, higher activities and productivities compared with the prior art, which, in addition, can be customised to the particular application needs.

The examples given below are intended to illustrate the subject-matter of the present invention in greater detail. However, they are not suitable for restricting the subject-matter of the invention to the given examples since, on the basis of the given information, the more general validity of the described subject-matter of the invention is disclosed to the person skilled in the art.

EXAMPLES

Synthesis of the Oxygen-Stabilised Organoaluminium Complexes

Example 1

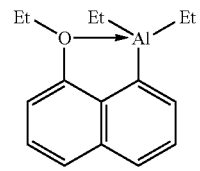

2.5 ml (20 mmol) of $Et_2AlCl$ are added dropwise at $-40°$ C. to a suspension of 50 ml of diethyl ether and 3.5 g (20 mmol) of (1-ethoxynaphth-1-yl)lithium, prepared from 33 ml (56 mmol) of t-butyllithium (1.7M solution in pentane) and 9.7 g (56 mmol) of 1-ethoxynaphthalene in 200 ml of hexane. The mixture is slowly brought to room temperature and stirred at room temperature for 24 h. The mixture is subsequently decanted off from the solid, the solvent is removed, the residue is taken up in 35 ml of toluene and filtered through a D4 frit. After removal of the toluene, fractional distillation gives (8-ethoxynaphth-1-yl)diethylaluminium as pale-yellow liquid having a boiling point of $146°$ C. at 0.01 mbar.

$^1$H NMR (benzene-$d_6$, 200.1 MHz): δ 0.36 ($ABX_3$, 2H, $^3J=8.2$ Hz, $^2J=14.5$ Hz, $(MeCHH')_2Al$), 0.41 ($ABX_3$, 2H, $^3J=8.2$ Hz, $^2J=14.5$ Hz, $(MeCHH')_2Al$), 1.00 (t, 3H, $^3J=7.1$ Hz, $OCH_2CH_3$), 1.30 ($ABX_3$, 6H, $^3J=8.2$ Hz, $(CH_3CHH')_2$ Al), 3.92 (q, 2H, $^3J=7.1$ Hz, $OCH_2CH_3$), 6.22 (dd, 1H, $^3J=7.7$ Hz, $^4J=0.7$ Hz, $H^7$), 7.03 (dd, 1H, $^3J=8.4$ Hz, $^3J=7.7$ Hz, $H^6$), 7.38 (dd, 1H, $^3J=8.4$ Hz, $^4J=0.7$ Hz, $H^5$), 7.45 (dd, 1H, $^3J8.4=$Hz, $^3J6.4$ Hz, $H^3$), 7.59 (dd, 1H, $^3J=8.4$ Hz, $^4J=1.3$ Hz, $H^4$), 7.91 (dd, 1H, $^3J=6.4$ Hz, $^4J=1.3$ Hz, $H^2$).

$^{13}C\{^1H\}$ NMR (benzene-$d_6$, 50.32 MHz): δ 0.33 (br, $(CH_3CH_2)_2Al$), 8.91 $((CH_3CH_2)_2Al)$, 12.85 ($OCH_2CH_3$), 66.41 ($OCH_2CH_3$), 102.81 ($C^7$), 123.33 ($C^5$), 123.71 ($C^6$), 125.28 ($C^4$), 127.45 ($C^3$), 132.39 ($C^{10/9}$), 133.17 ($C^{9/10}$), 133.59 ($C^2$), 144.9 (br, $C^1$), 153.27 ($C^8$).

$^{27}$Al NMR (benzene-$d_6$, 104.26 MHz): δ 189 ($w_{1/2}=8200$ Hz).

MS ($60°$ C.; m/z (%)): 256 (2) $[M]^+$, 227 (100) $[M-C_2H_5]^+$, 199 (56) $[M-(C_2H_5)-(C_2H_4)]^+$, 198 (23) $[M-(C_2H_5)_2]^+$, 171 (25) $[M-Al(C_2H_5)_2]^+$, 170 (36) $[M-(C_2H_5)_2-(C_2H_4)]^+$, 144 (17) $[C_{10}H_8O]^+$, 116 (4) $[C_9H_8]^+$, 115 (8) $[C_9H_7]^+$.

Analysis [%]: calculated for $C_{16}H_{21}AlO$ (256.32 g/mol) C, 74.97; H, 8.26. Found C, 74.71; H, 8.05.

Example 2

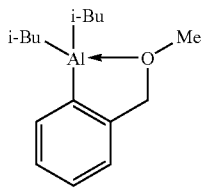

10.1 ml (50.2 mmol) of $^i$Bu$_2$AlCl are added dropwise at −78° C. to a suspension of 100 ml of toluene and 6.43 g (50.2 mmol) of (1-methoxymethylphen-2-yl)-lithium, prepared from 50.2 ml (50.2 mmol) of n-butyllithium (15% solution in hexane) and 10.1 g (50.2 mmol) of 1-bromo-2-methoxymethylbenzene in 100 ml of heptane. The mixture is slowly brought to room temperature and stirred at room temperature for 18 h. The mixture is subsequently filtered through a D4 frit. After removal of the toluene, fractional distillation gives (2-methoxymethylphen-1-yl)diisobutylaluminium as colourless, viscous liquid having a boiling point of 120° C. at 0.8 mbar.

$^1$H NMR (benzene-d$_6$, 200.1 MHz): δ 0.22 (ABX, 2H, $^3$J=6.9 Hz, $^2$J=14.0 Hz, (Me$_2$CHCHH')$_2$Al), 0.33 (ABX, 2H, $^3$J=6.9 Hz, $^2$J=14.0 Hz, (Me$_2$CHCHH')$_2$Al), 1.12 (d, 12H, $^3$J=6.5 Hz, ((CH$_3$)$_2$CHCH$_2$)$_2$Al), 2.03 (ABX, 2H, $^3$J=6.5 Hz, $^3$J=6.9 Hz, (Me$_2$CHCH$_2$)$_2$Al), 2.88 (s, 3H, OCH$_3$), 4.17 (s, 2H, C$_6$H$_4$CH$_2$O), 6.58–6.74 (m, 1H, H$^{ar}$), 7.11–7.26 (m, 2H, H$^{ar}$), 7.77–7.84 (m, 1H, H$^{ar}$).

$^{13}$C{$^1$H} NMR (benzene-d$_6$, 50.32 MHz): δ 22.7 (br, ((CH$_3$)$_2$CHCH$_2$)$_2$Al), 26.83 (((CH$_3$)$_2$CHCH$_2$)$_2$Al), 28.51 (((CH$_3$C'H$_3$)CHCH$_2$)$_2$Al), 28.62 (((CH$_3$C'H$_3$)CHCH$_2$)$_2$Al), 58.40 (OCH$_3$), 80.64 (C$_6$H$_4$CH$_2$O), 120.81 (C$^{ar}$), 126.91 (C$^{ar}$), 126.98 (C$^{ar}$), 136.47 (C$^{ar}$), 141.57 (C$^2$), 148.6 (br, C$^1$).

$^{27}$Al NMR (benzene-d$_6$, 104.26 MHz): δ 182 (w$_{1/2}$=7400 Hz).

MS (29° C.; m/z (%)): 205 (89) [M-C$_4$H$_9$]$^+$, 149 (100) [M-C$_4$H$_9$—C$_4$H$_8$]$^+$, 119 (32) [C$_7$H$_8$Al]$^+$, 91 (31) [C$_7$H$_7$]$^+$.

Analysis [%]: calculated for C$_{16}$H$_{27}$AlO (262.37 g/mol) C, 73.25; H, 10.37. Found C, 72.97; H, 10.26.

Example 3

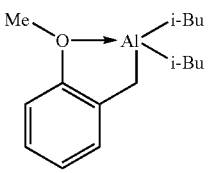

150 ml (39 mmol) of (2-methoxybenzyl)magnesium chloride as 0.26 molar solution are added dropwise over the course of 3 hours at 0° C. to 6.83 g (38.7 mmol) of $^i$Bu$_2$AlCl in 250 ml of tetrahydrofuran. The mixture is slowly brought to room temperature and stirred at room temperature for 18 h. The solvent is removed under reduced pressure (0.05 mbar), and the residue is suspended in 125 ml of n-pentane. The mixture is subsequently filtered through a D4 frit. After removal of the n-pentane, fractional distillation gives (2-methoxybenzyl)diisobutylaluminium as colourless, viscous liquid having a boiling point of 85° C. at 0.05 mbar.

$^1$H NMR (benzene-d$_6$, 200.1 MHz): δ 0.22 (d, 4H, $^3$J=6.9 Hz, (Me$_2$CHCH$_2$)$_2$Al), 1.07 (d, 12H, $^3$J=6.5 Hz, ((CH$_3$)$_2$CHCH$_2$)$_2$Al), 1.45 (s, 1H, C$_6$H$_4$CHH'Al), 1.46 (s, 1H, C$_6$H$_4$CHH'Al), 1.99 (tsp, 2H, $^3$J=6.5 Hz, $^3$J=6.9 Hz, (Me$_2$CHCH$_2$)$_2$Al), 3.18 (s, 3H, OCH$_3$), 6.20–6.25 (m, 1H, H$^{ar}$), 6.75–6.90 (m, 2H, H$^{ar}$) 7.20–7.30 (m, 1H, H$^{ar}$).

$^{13}$C{$^1$H} NMR (benzene-d$_6$, 50.32 MHz): δ 10.3 (br, C$_6$H$_4$CH$_2$Al), 22.3 (br, ((CH$_3$)$_2$CHCH$_2$)$_2$Al), 26.74 (((CH$_3$)$_2$CHCH$_2$)$_2$Al), 28.44 (((CH$_3$)$_2$CHCH$_2$)$_2$Al), 55.78 (OCH$_3$), 109.20 (C$^{ar}$), 124.22 (C$^{ar}$), 125.06 (C$^{ar}$), 133.98 (C$^{ar}$), 134.57 (C$^1$), 155.62 (C$^2$).

$^{27}$Al NMR (benzene-d$_6$, 104.26 MHz): δ 195 (w$_{1/2}$=7300 Hz).

MS (65° C.; m/z (%)): 262 (1) [M]$^+$, 205 (80) [M-C$_4$H$_9$]$^+$, 149 (100) [M-C$_4$H$_9$—C$_4$H$_8$]$^+$, 134 (16) [C$_7$H$_7$AlO]$^+$ 91 (10) [C$_7$H$_7$]$^+$.

Analysis [%]: calculated for C$_{16}$H$_{27}$AlO (262.37 g/mol) C, 73.25; H, 10.37. Found C, 72.61; H, 10.44.

Example 4

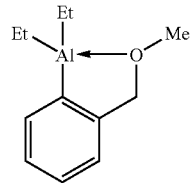

A 1 molar n-hexane solution of diethylaluminium chloride (60.4 ml, 60.4 mmol) are slowly added at −50° C. to a suspension of [2-(methoxymethyl)-phenyl]lithium (7.74 g, 60.4 mmol) in 120 ml of toluene. The mixture is brought to room temperature and stirred at 60° C. for 2 days. The solvent is removed under reduced pressure, and the residue is taken up in 100 ml of toluene. The mixture is subsequently filtered through a D4 frit. After removal of the toluene, fractional distillation gives (2-methoxymethylphen-1-yl)-diethylaluminium as colourless, viscous liquid having a boiling point of 108° C. at 0.71 mbar.

$^1$H NMR (benzene-d$_6$, 200.1 MHz): δ 0.24 (q, 4H, $^3$J=8.2 Hz, (CH$_3$CH$_2$)$_2$Al), 1.26 (q, 6H, $^3$J=8.2 Hz, (CH$_3$CH$_2$)$_2$Al), 2.88 (s, 3H, OCH$_3$), 4.16 (s, 2H, C$_6$H$_4$CH$_2$O), 6.67–6.78 (m, 1H, H$^{ar}$), 7.12–7.26 (m, 2H, H$^{ar}$), 7.71–7.80 (m, 1H, H$^{ar}$).

$^{13}$C{$^1$H} NMR (benzene-d$_6$, 50.32 MHz): δ 0.12 (br, (CH$_3$CH$_2$)$_2$Al), 9.69 ((CH$_3$CH$_2$)$_2$Al), 58.54 (OCH$_3$), 81.09 (C$_6$H$_4$CH$_2$O), 120.87 (C$^{ar}$), 126.86 (C$^{ar}$), 127.04 (C$^{arl}$) 136.43 (C$^{ar}$), 142.16 (C$^2$), 147.2 (br, C$^1$).

$^{27}$Al NMR (benzene-d$_6$, 104.26 MHz): δ 184 (w$_{1/2}$=5000 Hz).

MS (49° C.; m/z (%)): 177 (100) [M-C$_2$H$_5$]$^+$, 149 (56) [M-C$_2$H$_5$—C$_2$H$_4$]$^+$, 119 (34) [C$_7$H$_8$Al]$^+$, 91 (29) [C$_7$H$_7$]$^+$.

Analysis [%]: calculated for C$_{12}$H$_{19}$AlO (206.26 g/mol) C, 69.88; H, 9.28. Found C, 69.51; H, 9.05.

Example 5

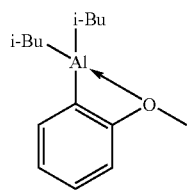

Diisobutylaluminium chloride (10.65 g, 60.3 mmol) is slowly added at −60° C. to a suspension of [2-(methoxy) phenyl]lithium (6.87 g, 60.3 mmol) in 120 ml of toluene. The mixture is brought to room temperature and stirred for 12 hours. The suspension is filtered through a D4 frit. The solvent is removed, and the residue is suspended in n-heptane. The suspension is passed through a frit, and the solid is washed twice with 20 ml of n-heptane.

Recrystallisation of the solid from toluene at 0° C. gives [2-(methoxy)-phen-1-yl]diisobutylaluminium as colourless crystals having a melting point of 128° C.

$^1$H NMR (THF-$d_8$, 400.1 MHz): δ 0.16 (d, 4H, $^3J$=7.1 Hz, (Me$_2$CHCH$_2$)$_2$Al), 0.91 (d, 12H, $^3J$=6.0 Hz, ((CH$_3$)$_2$CHCH$_2$)$_2$Al), 1.89 (tsp, 2H, $^3J$=6.0 Hz, $^3J$=7.1 Hz, (Me$_2$CHCH$_2$)$_2$Al), 3.70 (s, 3H, OCH$_3$), 6.69 (d, 1H, $^3J$=8.1 Hz, H$^3$), 6.77 (dd, 1H, $^3J$=6.8 Hz, $^3J$=7.3 Hz, H$^5$), 7.10 (ddd, 1H, $^3J$=8.1 Hz, $^3J$=7.3 Hz, $^4J$=1.9 Hz, H$^4$), 7.39 (dd, 1H, $^3J$=6.8 Hz, $^4J$=1.9 Hz, H$^6$).

$^{13}$C{$^1$H} NMR (THF-$d_8$, 100.64 MHz): δ 22.77 (br, ((CH$_3$)$_2$CHCH$_2$)$_2$Al), 27.43 (((CH$_3$)$_2$CHCH$_2$)$_2$Al), 28.88 (((CH$_3$)$_2$CHCH$_2$)$_2$Al), 54.66 (OCH$_3$), 108.60 (C$^3$), 120.99 (C$^5$), 129.04 (C$^4$), 139.27 (C$^6$), 139.5 (br, C$^1$), 167.22 (C$^2$).

$^{27}$Al NMR (THF-$d_8$, 104.26 MHz): δ 176 ($w_{1/2}$=7200 Hz); (benzene-$d_6$, 104.26 MHz): δ 220 ($w_{1/2}$=19500 Hz).

MS (86° C.; m/z (%)): 191 (72) [M-C$_{15}$H$_{25}$AlO—C4H$_9$]$^+$, 135 (100) [C$_{15}$H$_{25}$AlO—C$_4$H$_9$—C$_4$H$_8$]$^+$, 108 (20) [C$_7$H$_8$O]$^+$, 105 (26) [C$_6$H$_6$Al]$^+$, 78 (16) [C$_6$H$_6$]$^+$, 65 (11) [C$_5$H$_5$]$^+$.

Analysis [%]: calculated for C$_{30}$H$_{50}$Al$_2$O$_2$ (496.68 g/mol) C, 72.55; H, 10.15. Found C, 72.16; H, 9.87.

Cryoscopic molecular weight determination in benzene: 376 g/mol.

Example 6

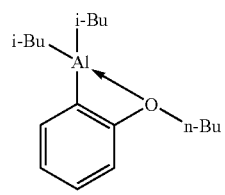

Diisobutylaluminium chloride (11.25 g, 63.7 mmol) is slowly added at −60° C. to a 0.41 molar suspension of [2-(butoxy)phenyl]lithium (161 ml, 66.5 mmol) and n-heptane. The mixture is brought to room temperature and stirred for 12 hours. The solvent is removed, and the residue is suspended in 100 ml of toluene. The suspension is passed through a D4 frit. After removal of the toluene, fractional distillation gives [2-(butoxy)phen-1-yl]diisobutylaluminium as colourless, viscous liquid having a boiling point of 74° C. at 0.48 mbar.

Ethylene Polymerisation:

All polymerisations were carried out under an argon inert-gas atmosphere using Schlenk techniques. Solid catalyst and cocatalyst components were weighed out in a Braun labmaster 130 Glovebox using an analytical balance. The catalyst employed was TiCl$_4$, supported on MgCl$_2$, in the form of a 0.1 molar suspension. The cocatalyst was weighed out in a 25 ml glass flask and employed for the polymerisation as hexane solution.

The polymerisations were carried out in a Büchi 1 l glass autoclave. Before each experiment, the reactor was cleaned using ethanol and toluene, hexane or heptane, evacuated at 95° C. for one hour in an oilpump vacuum and flushed repeatedly with argon in between. The autoclave was filled with 195 ml of hexane and with the catalyst suspension. A temperature of 60° C. was set. The monomer was injected with a pressure of 2 bar. After saturation of the suspension located in the reactor with the monomer, the polymerisations were initiated by injection of a hexane solution of the cocatalyst. Isobaric performance of the reaction was ensured by the monomer supply of the reactor, consisting of a Brooks PC8606 pressure regulator and a Brooks 5850TR mass flow controller. The monomer consumption was recorded by means of a Brooks model 5876 control and display unit and a personal computer fitted with an A/D converter card connected thereto, with the aid of the RTX View software.

The polymerisations were terminated by injection of 5 ml of ethanol. Dilute hydrochloric acid was added to the polymerisation suspension, which was stirred overnight. The organic phase was neutralised using a saturated sodium hydrogencarbonate solution and washed with water. The polymer was dried to constant weight in an oil-pump vacuum.

Further experimental results carried out under identical or similar conditions are shown in Table 1. This table also contains experiments carried out in the presence of an aluminium cocatalyst according to the invention and TiCl$_4$/MgCl$_2$ as catalyst.

TABLE 1

| Reaction conditions: | |
| --- | --- |
| Ethylene pressure: | 2 bar, |
| Reaction temperature: | 60° C., |
| Reaction time: | 60 minutes, |
| Catalyst concentration: | TiCl$_4$:5.3 10$^{-4}$ mol/l, |
| Catalyst/cocatalyst ratio | 20 |
| Solvent | hexane |
| Solvent volume | 200 ml |

The results for polymerisations of ethylene in the presence of the organoaluminium complexes prepared in Examples 1 to 6 as cocatalysts compared with Et3Al are shown in FIG. 1.

TABLE 2

| (2-Methoxymethylphen-1-yl)diethylaluminium | | | | |
| --- | --- | --- | --- | --- |
| Al/Ti | Activity [kg/(mol$_{Ti}$ · mol/l)] | $T_m$ [° C.] | Crystallinity [%] | $M_\eta$ [g/mol] |
| 3 | 980 | 141 | 61 | 1,900,000 |
| 5 | 1134 | 143 | 63 | 1,600,000 |
| 10 | 3122 | 138 | 63 | 1,500,000 |

TABLE 2-continued

| (2-Methoxymethylphen-1-yl)diethylaluminium | | | | |
|---|---|---|---|---|
| Al/Ti | Activity [kg/(mol$_{Ti}$ · mol/l)] | T$_m$ [° C.] | Crystallinity [%] | M$_n$ [g/mol] |
| 20 | 4090 | 136 | 56 | 1,800,000 |
| 50 | 5600 | 138 | 60 | 1,600,000 |
| 75 | 6020 | 137 | 55 | 1,500,000 |

The invention claimed is:

1. A compound of formula (I)

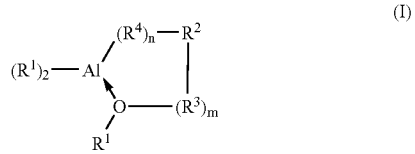

in which

R$^1$ is, in each case independently of one another, a branched or unbranched C$_1$–C$_7$-alkyl, -cycloalkyl, -alkenyl, -cycloalkenyl, -aryl or -alkynyl;

R$^2$ is

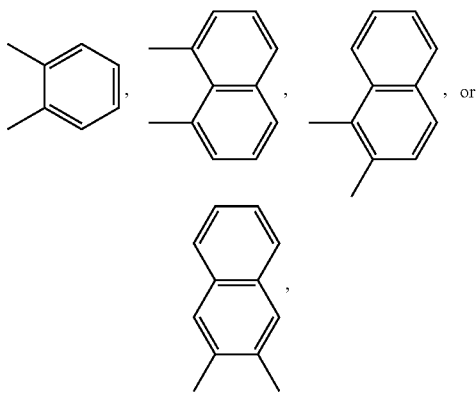

which is unsubstituted, or mono- or polyalkylated and/or mono- or polyfluorinated;

R$^3$ and R$^4$ are, independently of one another, CH$_2$, CF$_2$ or C(R$^1$)$_2$;

m is 0, 1 or 2, and n is 0, 1 or 2.

2. A compound according to claim 1, which is (8-Ethoxynaphth-1-yl)diethylaluminium, (2-methoxymethyl)phen-1-yl)diethylaluminium, (2-methoxymethylphen-1-yl)diisobutylaluminium, (2-methoxybenzyl)diisobutylaluminium, [2-(methoxy)phen-1-yl]diisobutylaluminium, [2-(butoxy)phen-1-yl]diisobutylaluminium.

3. A coordination catalyst system comprising as a cocatalyst, a compound according to claim 2.

4. A coordination catalyst system comprising as a cocatalyst, a compound of formula (I) according to claim 1.

5. A coordination catalyst system according to claim 4, which comprises a Ziegler-Natta catalyst.

6. A coordination catalyst system according to claim 4, which comprises a transition-metal compound of sub-group IV to VIII of the Periodic Table of the Elements.

7. A coordination catalyst system according to claim 4, which comprises a transition-metal compound of TiCl$_4$ or VCl$_4$.

8. A coordination catalyst system according to claim 4, which comprises a transition-metal compound of TiCl$_4$, which is supported on MgCl$_2$, or VCl$_4$, which is supported on MgCl$_2$.

9. In a process for the preparation of polymers by polymerisation, wherein the improvement is that said polymerization is carried out in the present of a coordination catalyst system according to claim 4.

10. A process according to claim 9, wherein polyethylene is prepared.

11. A process according to claim 9, wherein high-molecular-weight polyethylene is prepared.

12. The process for preparing a compound of formula (I) according to claim 1, comprising reacting an alkoxyarylmetal compound with a dialkylaluminium chloride, wherein the alkoxyarylmetal compound to dialkylaluminium chloride molar ratio is 1:1.

13. A process according to claim 12, comprising
 a) mixing together an alkoxyarylmetal compound, suspended in a hydrocarbon, diethyl ether or tetrahydrofuran, with an equimolar amount of a dialkylaluminium chloride, dissolved in a hydrocarbon, at a temperature of +20 to −78° C., and
 b) stirring the mixture at a temperature of 20 to 80° C. for 2 to 60 hours, removing the hydrocarbon, diethyl ether or tetrahydrofuran, and optionally separating a compound of formula I by distillation or crystallisation.

14. A process according to claim 12, wherein the alkoxyarylmetal compound is an alkoxyaryllithium or alkoxyaryl-Grignard compound.

* * * * *